(12) United States Patent
Bishop et al.

(10) Patent No.: US 12,105,092 B2
(45) Date of Patent: Oct. 1, 2024

(54) MOLECULARLY IMPRINTED PARTICLES

(71) Applicant: GEORGE MASON UNIVERSITY, Fairfax, VA (US)

(72) Inventors: Barney Bishop, Annandale, VA (US); Mrinalini Ramanan, Fairfax, VA (US); Yaling Zhu, Gaithersburg, MD (US)

(73) Assignee: George Mason University, Fairfax, VA (US)

( * ) Notice: Subject to any disclaimer, the term of this patent is extended or adjusted under 35 U.S.C. 154(b) by 737 days.

(21) Appl. No.: 16/872,661

(22) Filed: May 12, 2020

(65) Prior Publication Data

US 2020/0363421 A1    Nov. 19, 2020

Related U.S. Application Data

(60) Provisional application No. 62/847,978, filed on May 15, 2019.

(51) Int. Cl.
*G01N 33/58*    (2006.01)
*C08F 220/56*    (2006.01)
*C08F 220/58*    (2006.01)

(52) U.S. Cl.
CPC ......... *G01N 33/582* (2013.01); *C08F 220/56* (2013.01); *C08F 220/58* (2013.01); *C08F 2438/03* (2013.01); *G01N 2600/00* (2013.01)

(58) Field of Classification Search
CPC ............. G01N 33/582; G01N 2600/00; G01N 21/6428; G01N 21/6408; G01N 2021/6432; C08F 220/56; C08F 220/58; C08F 2438/03; C08F 265/10; C08F 220/54; C08F 265/06; C08F 285/00; C08F 222/385; C08F 222/102; C08F 220/365

See application file for complete search history.

(56) References Cited

U.S. PATENT DOCUMENTS

| | | | |
|---|---|---|---|
| 7,344,752 B2 | 3/2008 | Zheng et al. | |
| 8,133,411 B2 | 3/2012 | Charreyre et al. | |
| 9,173,943 B2 * | 11/2015 | Hoshino | C07K 1/22 |
| 10,053,531 B2 * | 8/2018 | Zhang | C08F 220/06 |
| 2012/0004381 A1 | 1/2012 | Rizzardo et al. | |
| 2015/0299366 A1 | 10/2015 | Zhang et al. | |

FOREIGN PATENT DOCUMENTS

EP    1950232 A1    7/2008

OTHER PUBLICATIONS

Chen et al. Molecularly Imprinted Polymers with Stimuli-Responsive Affinity: Progress and Perspectives. Polymers 2015, vol. 7, pp. 1689-1715. (Year: 2015).*
Ali et al. Utilizing fluorescein methacrylate as fluorescent functional monomer on synthesizing fluorescent molecularly imprinted polymer in sensing caffeine. National Symposium of Polymeric Materials 2018, AIP Con. Proc. 1985, AIP publishing, pp. 1-11 (Year : 2018).*
Grazon et al. One-Pot Synthesis of Pegylated Fluorescent Nanoparticles by RAFT Miniemulsion Polymerization Using a Phase Inversion Process. Macromolecular Rapid Communications 2011, vol. 32, pp. 699-705. (Year: 2011).*
Grazon et al. Fluorescent core-shell nanoparticles and nanocapsules using comb-like macromolecular RAFT agents: synthesis and functionalization thereof. Polym. CHem. 2016, vol. 7, pp. 4272-4283. (Year: 2016).*
Huang et al. Synthesis of amphiphilic fluorescent polymers via a one-pot combination of multicomponent Hantzsch reaction and RAFT polymerization and their cell imaging applications. Polym. Chem. 2017, vol. 8, pp. 4805-4810. (Year: 2017).*
Mohammadi, Reza. Molecularly Imprinted Core-Shell Nanoparticles by Surface Initiated RAFT Polymerization. Thesis for the degree of Doctor of Philosophy in Chemistry, Faculty of Chemistry and Chemical Biology at the Technical University of Dortmund, Germany, Jun. 2014, pp. 1-232. (Year: 2014).*
Robin et al. Strategies for preparing fluorescently labelled polymer nanoparticles. Polym Int 2015, vol. 64, pp. 174-182. (Year: 2015).*
Burns et al., "Fluorescent core-shell silica nanoparticles: towards "Lab on a Particle" architectures for nanobiotechnology", Chem. Soc. Rev., 2006, vol. 35, p. 1028-1042.
Chen et al., "Molecular imprinting: perspectives and applications", Chem. Soc. Rev., 2016, vol. 45, p. 2137-2211.
Chen et al., "Molecularly Imprinted Polymers with Stimuli-Responsive Affinity: Progress and Perspectives", Polymers, 2015, vol. 7, p. 1689-1715.
Le Goff et al., "Hydrogel microparticles for biosensing", Eur Polym J., Nov. 2015, vol. 72, p. 386-412.
Lunn et al., "Established and Emerging Strategies for Polymer Chain-End Modification", Journal of Polymer Science, Part A: Polymer Chemistry, 2017, p. 1-12.
Moad et al., "Living Radical Polymerization by the RAFT Process—A First Update", Aust. J. Chem., 2006, vol. 59, p. 669-692.
Ow et al., "Bright and Stable Core-Shell Fluorescent Silica Nanoparticles", Nano Letters, 2005, vol. 5, No. 1, p. 113-117.
Ribeiro et al., "Preparation of Well-Dispersed Chitosan/Alginate Hollow Multilayered Microcapsules for Enhanced Cellular Internalization", Molecules, 2018, vol. 23, No. 625, p. 1-16.
Rizzardo et al., "On the Origins of Nitroxide Mediated Polymerization (NMP) and Reversible Addition-Fragmentation Chain Transfer (RAFT)", Aust. J. Chem., 2012, vol. 65, p. 945-969.
Wang et al., "Droplet Microfluidics for the Production of Microparticles and Nanoparticles", Micromachines, 2017, vol. 8, No. 22, p. 1-23.
Wang et al., "Volume labeling with Alexa Fluor dyes and surface functionalization of highly sensitive fluorescent silica (SiO2) nanoparticles", Nanoscale, 2013, vol. 5, p. 10369-10375.
Zhang et al., "'One Pot' Synthesis of Well-defined Poly(aminophosphonate)s: Time for Kabachnik-Fields Reaction on Stage of Polymer Chemistry", Electronic Supplementary Material (ESI) for Polymer Chemistry, total 3 pages.

(Continued)

*Primary Examiner* — Shafiqul Haq (74) *Attorney, Agent, or Firm* — Saul Ewing LLP; Alireza Behrooz (57) ABSTRACT

Molecularly imprinted particles comprising a label are described herein, in particular such particles prepared by RAFT polymerization, as are compositions and kits comprising such particles, and methods for preparing and using such particles.

12 Claims, 7 Drawing Sheets

(56) References Cited

OTHER PUBLICATIONS

Zhou et al., "Molecularly imprinted polymer beads for nicotine recognition prepared by RAFT precipitation polymerization: a step forward towards multi-functionalities", RSC Adv., 2014, vol. 4, p. 30292-30299.

Xie, et al. "Synthesis of magnetic molecularly imprited polymers by reversible addition fragementation chain transfer strategy and its application in the Sudan dyes residue analysis." Journal of Chromatography A, 1405 (2015) 32-39.

* cited by examiner

MOLECULARLY IMPRINTED PARTICLES

CROSS-REFERENCE TO RELATED APPLICATION

This non-provisional application claims the benefit under 35 U.S.C. § 119(e) to U.S. Provisional Application No. 62/847,978, filed on May 15, 2019, which is hereby expressly incorporated by reference into the present application.

FIELD OF THE INVENTION

The present invention relates to molecularly imprinted particles comprising a label, and to compositions, methods, and kits relating thereto.

BACKGROUND

Microparticles having a detectable label have previously employed multi-step, post-synthesis covalent modifications to produce polymeric particles, or, used covalent modifications during synthesis to produce labeled nanoparticles. For example, silica-based fluorescent nanoparticles that use a covalent incorporation of fluorophores into the non-polymeric particle matrix have been previously described as well as hydrogel polymer particles that covalently attach fluorophores for various applications.

There is a need for new and effective particles comprising a label, as well as for versatile methods for preparing them for use in a variety of applications.

SUMMARY OF THE INVENTION

In one aspect, the present invention provides a molecularly imprinted particle comprising a core formed by a crosslinked polymer network. The core comprises a detectable label.

In another aspect, the present invention provides a method for preparing a molecularly imprinted particle comprising a core formed by crosslinked polymer networks. The method comprises performing a reversible addition-fragmentation chain transfer (RAFT) polymerization of a composition to form the core, wherein the composition comprises a functional monomer susceptible to free-radical polymerization; and a label.

In some aspects, the present invention provides a composition comprising a molecularly imprinted particle comprising a core formed by a crosslinked polymer network. The core comprises a detectable label.

In other aspects, the present invention provides a kit comprising a molecularly imprinted particle; and instructions. The molecularly imprinted particle comprises a core formed by a crosslinked polymer network. The core comprises a detectable label.

In one aspect, the present invention provides a method for capturing or detecting an analyte. The method comprises contacting the analyte with a molecularly imprinted particle. The molecularly imprinted particle comprises a core formed by a crosslinked polymer network. The core comprises a detectable label. The particle further comprises a functionality at an outer layer of the particle for capturing or detecting the analyte.

In another aspect, the present invention provides a method for detecting an environmental change. The method comprises exposing a molecularly imprinted particle to the environmental change. The molecularly imprinted particle comprises a core formed by a crosslinked polymer network. The core comprises a detectable label. The particle further comprises a functionality at an outer layer of the particle. The functionality comprises a reporter for detection of the environmental change.

DETAILED DESCRIPTION OF THE INVENTION

In one aspect, the present invention provides a molecularly imprinted particle comprising a core formed by a crosslinked polymer network, wherein said core comprises a detectable label.

In some embodiments, the core of the particle further has a molecularly imprinted cavity comprising the label.

In one embodiment, the cavity is complementary to the label in size, shape and/or spatial arrangement.

In another embodiment, the crosslinked polymer network comprises polymerized functional monomers.

In some embodiments, the polymerized functional monomers have a complementary conformation to the label.

In other embodiments, the cavity or the complementary conformation comprise interactive moieties that can interact with a positionally corresponding moiety on the label to form a bond or other attractive association, such as, for example, an electrostatic, covalent, ionic, hydrophobic, hydrogen-bonding, or other interaction.

In one embodiment, the polymerized functional monomers are formed by polymerization of a functional monomer.

Examples of functional monomers include, but are not limited to, vinyl monomers, allyl monomers, acetylenes, acrylates, methacrylates, acrylamides, methacrylamides, chloroacrylates, itaconates, and trifluoromethylacrylates.

In one embodiment, the functional monomer is $C_2$-$C_8$ monoolefin, aromatic vinyl compounds, heterocyclic aromatic vinyl compounds, monoolefin type unsaturated carboxylic acid, carboxylate, ester and amide, vinyl alcohol or ester thereof, allyl alcohol or ester thereof, vinyl ether, vinyl lactam, vinyl halide, 1,1-dihaloethylene, (meth)acrylic acid or ester, salt, or amide thereof, 4-vinylpyridine, 2-vinylpyridine, 4-vinylbenzoic acid, (meth)acrylic acid, trifluoromethylacrylic acid, 2-hydroxyethyl methacrylate, dimethylaminoethyl methacrylate, (meth)acrylamide, 2-acrylamido-2-methylpropanesulfonic acid, 4-vinylimidazole, itaconic acid or N-vinylpyrrolidone.

In another embodiment, the functional monomer is 4-vinylpyridine, 2-vinylpyridine, 4-vinylbenzoic acid, (meth)acrylic acid, trifluoromethyl acrylic acid, 2-hydroxyethyl methylacrylate, dimethylaminoethyl methacrylate, (meth)acrylamide, 2-acry lamido-2-methy 1-1-propanesulfonic acid, 4-vinylimidazole, itaconic acid or N-vinylpyrrolidone.

In another embodiment, the functional monomer comprises a vinyl functional monomer.

In some embodiments, the functional monomer comprises N-tert-Butylmethacrylamide (tBMAm).

As used herein, the term "label" refers to a molecule or moiety having a property or characteristic that is capable of detection. Exemplary labels include but are not limited to luminescent agents, radioactive isotopes (e.g., $H^3$, $Ba^{133}$, $C^{13}$, $Ca^{45}$, $Cr^{51}$, $Cs^{137}$, $Eu^{152}$, $Fe^{59}$, $I^{125}$, $Ni^{63}$, $P^{32}$, $P^{33}$, $Ra^{226}$, $S^{35}$, technetium 99, thallium 201, $Xe^{133}$), stains, dyes, proteins, and enzymes.

The term "signal" refers to the property or characteristic of the label that permits it to be visually or instrumentally detected and/or distinguished. Exemplary signals include but are not limited to fluorescent signals, chemiluminescent signals, radioactive signals, chromogenic signals, and the like.

In some embodiments, the label is directly detectable ("directly detectable label"), as with, for example, fluorophores, radioisotopes, chemiluminophores, enzymes, colloidal particles, fluorescent microparticles and the like; or a label may be indirectly detectable ("indirectly detectable label"), as with, for example, specific binding members (e.g., a protein tag that binds a fluorogenic ligand (so-called fluorogen) and activates its fluorescence, wherein the fluorogenic ligand is nonfluorescent by its own and becomes fluorescent only upon binding its cognate tag; See e.g., U.S. Pat. No. 10,138,278; Plamont, M. et al., PNAS, 113:497-502 (2016), each of which is herein incorporated by reference in its entirety).

It will be understood that directly detectable labels may require additional components such as, for example, substrates, triggering reagents, light, and the like to enable detection of the label.

In some embodiments, the label is a directly detectable label.

When indirectly detectable labels are used, they can be used in combination with a specific binding member that is a directly detectable label or a "conjugate."

In some embodiments, the label is an indirectly detectable label that can be used in combination with a directly detectable label e.g., a fluorogenic ligand (so-called fluorogen).

A conjugate is typically a specific binding member which has been attached or coupled to a directly detectable label. Coupling chemistries for synthesizing a conjugate are well known in the art and can include, for example, any chemical and/or physical interaction/reaction that does not destroy the specific binding property of the specific binding member or the detectable property of the label.

As used herein, "specific binding member" refers to a member of a binding pair, i.e., two different molecules where one of the molecules through, for example, chemical or physical interactions specifically interacts with or binds to the other molecule. In addition to protein tag and fluorogenic ligand specific binding pairs (e.g., a protein tag that binds a fluorogen and activates its fluorescence, wherein the fluorogenic ligand is nonfluorescent by its own and becomes fluorescent only upon binding its cognate tag), other specific binding pairs include, but are not intended to be limited to, antigen and antibody; avidin/streptavidin and biotin; haptens and antibodies specific for haptens; complementary nucleotide sequences; enzyme cofactors or substrates and enzymes; and the like.

Exemplary binding pairs, i.e., two different molecules where one of the molecules through, for example, chemical or physical interactions specifically interacts with or binds to the other molecule and activates its fluorescence include but are not limited to those described by e.g., Schwartz, S. L. et al., ACS Chem. Biol., 10:539-546 (2015) (Epub. 2014 Nov. 24) and Szent-Gyorgyi, C. et al., Nat. Biotechnol., 26:235-240 (2008), each of which is incorporated by reference in its entirety. For example, fluorogen activating proteins (FAPs) are genetically expressible single-chain antibody fragments with molecular recognition properties for cognate dye partners termed fluorogens. Without wishing to be bound by any particular theory, it is believed that binding of fluorogen to the FAP restricts molecular rotations around double bonds in the fluorogen structure and results in significant enhancements in extinction coefficient and fluorescence quantum yield. Id. This process is fully reversible, and unbound fluorogen, even if previously bound, is essentially nonfluorescent. Id.

In some embodiments, the label is a small molecule.

The term "small molecule," as used herein, refers to a low molecular weight compound, which is not a polymer. The term encompasses molecules having a molecular weight of less than about 10,000 Daltons or less than about 9000 Daltons or less than about 8000 Daltons or less than about 7000 Daltons or less than about 6000 Daltons or less than about 5000 Daltons or less than about 4000 Daltons or less than about 3000 Daltons or less than about 2000 Daltons or less than about 1000 Daltons or less than about 900 Daltons or less than about 800 Daltons.

Luminescent labels emit light upon excitation by an external energy source and may be grouped into categories dependent upon the source of the exciting energy, including but not limited to fluorescent or photoluminescent labels that are excitable by units of electromagnetic radiation (photons) of infrared, visible, or ultraviolet light; radioluminescent labels deriving energy from high energy particles; chemiluminescent labels that obtain energy from chemical reactions; and bioluminescent labels wherein the exciting energy is supplied in a biological system. Fluorophores include, but are not limited to BODIPY, fluorescein, fluorescein substitutes (Alexa Fluor dye, Oregon green dye), long wavelength dyes, and UV-excited fluorophores. These and additional fluorophores are listed in Fluorescent and Luminescent Probes for Biological Activity, A Practical Guide to Technology for Quantitative Real-Time Analysis, Second Ed. W. T. Mason, ed. Academic Press (1999) (herein incorporated by reference).

In some embodiments, the label is a fluorescent label.

In other embodiments, the label is 4-fluoro-7-nitrobenzofurazan (NBD—F), 4-chloro-7-nitrobenzofurazan (NBD—Cl), 4-fluoro-7-nitro-[2,1,3]-benzoxadiazole (NBD), 5(6)-carboxyfluorescein N-hydroxysuccinimide ester (Fluorescein) or 5(6)-carboxytetramethylrhodamine N-succinimidyl ester (TAMRA).

In another embodiment, the label is fluorescein or a derivative thereof.

In one embodiment, the label is 2',7'-Dichlorofluorescein diacetate, 5(6)-Carboxyfluorescein diacetate, 5(6)-Carboxyfluorescein diacetate N-succinimidyl ester, 5-(Bromomethyl)fluorescein, 5-(Iodoacetamido)fluorescein, 5-([4,6-Dichlorotriazin-2-yl]amino)fluorescein hydrochloride, 5-Carboxy-fluorescein diacetate N-succinimidyl ester, 5-Carboxyfluorescein, 5-Carboxyfluorescein N-succinimidyl ester, 6-Carboxy-fluorescein diacetate N-succinimidyl ester, 6-[Fluorescein-5(6)-carboxamido]hexanoic acid, 6-[Fluorescein-5(6)-carboxamido]hexanoic acid N-hydroxysuccinimide ester, 6-Carboxy-4',5'-dichloro-2',7'-dimethoxyfluorescein N-hydroxysuccinimide ester, 6-Carboxyfluorescein, Eosin Y disodium salt, Fluorescein (free acid), Fluorescein 5(6)-isothiocyanate, Fluorescein diacetate 5(6)-isothiocyanate, Fluorescein diacetate 5-maleimide, Fluorescein diacetate 6-isothiocyanate, Fluorescein isothiocyanate isomer I, Fluorescein sodium salt, Fluorescein-5-EX N-hydroxysuccinimide ester, Fluorescein-O'-acetic acid, or O'-(Carboxymethyl)fluoresceinamide.

In other embodiments, the label is a quenchable label. In one embodiment, the label is a reversibly quenchable label.

The term "quench" or "quenching" is used to indicate a reduction in detectable emission of a signal, e.g., fluorescence, from the label.

In some embodiments, quenching is a reduction of at least about 50%, preferably at least about 60%, 70%, 80%, 90%, 95% or more, of the detectable signal from the label. In one embodiment, quenching is a reduction of 100% of the detectable signal of the label.

In other embodiments, the label is a reversibly quenchable fluorescent label capable of transitioning into a nonfluorescent state because of e.g., chromophore protonation. In this manner, the label can be (i) chemically quenched by an acid (e.g., hydrochloric acid (HCl)) or acidic buffer or environment; and (ii) chemically reactivated to its fluorescent state by e.g., a base (e.g., NaOH) or an alkaline buffer or environment.

In some embodiments, the label is Fluorescein-5-EX Succinimidyl Ester.

In still other embodiments, quenching or a quenching condition can include at least one quenching agent. The quenching agent can be any chemical, compound or biological molecule that can cause quenching of a signal, either alone or in combination with other agents or factors.

In some embodiments, a quenching agent (quencher) may be a molecule that absorbs the energy of an excited fluorophore. Without wishing to be bound by any particular theory, it is believed that proximity of a fluorophore and a quencher allow for the energy to be transferred from the fluorophore to the quencher. For example, by absorbing this energy, the quencher prevents the fluorophore from releasing the energy in the form of a photon, thereby preventing fluorescence.

In other embodiments, quenching agents may be categorized as non-fluorescent and fluorescent quenchers. Non-fluorescent quenchers can quench the fluorescence of a wide variety of fluorophores. Some non-fluorescent quenchers absorb energy from the fluorophore and release the energy as heat. Examples of non-fluorescent quenchers include but are not limited to HCl, ($Na_2S_2O_4$), 4-(4'-dimethylaminophenylazo)benzoic acid) (DABCYL), QSY-7, and QSY-33.

In one embodiment, the particle is a nanoparticle having a crosslinking degree of at least about 50%, preferably at least about 60%, 70%, 80%, 90%, 95% or more. In another embodiment, the crosslinking degree is 100%.

In another embodiment, the core has a core diameter of about 0.5 μm or less.

In some embodiments, core size distribution indices of the core as determined by dynamic light scattering (DLS) according to International Organization for Standardization (ISO) 22412 are about 0.6 μm or less, preferably less than or equal to about: 0.5, 0.4, 0.3, 0.2, and 0.1 μm.

In other embodiments, the particle is stable e.g., substantially free of breakdown products or degradants, in particular under formulation and extended storage conditions. In some embodiments, the particle remains stable over a period of at least about 4 months at 4° C.

In one embodiment, the particle further comprises a polymeric shell at least partially surrounding the core. Preferably, the polymeric shell comprises crosslinked units of a second monomer. In some embodiments, the polymeric shell is covalently connected to the core.

In one embodiment, the second monomer comprises N-methacryloyl-6-aminohexanoic acid (MA6AHA).

In some embodiments, the particle comprising the shell has a total combined particle/shell diameter of about 800 μm or less.

In another embodiment, during formation of the core by polymerization, the growing polymer chain can be exposed to one or more additional monomers and the polymerization continued. In this manner, the one or more additional monomers can introduce a new functionality into the polymer. Thus, in addition to the label, an extended polymer can be produced with affinity to a second template introduced into the system. For example, such an extended block polymer could have a functionality that would be useful in diagnostics, analyte capture and/or detection, and the like.

In some embodiments, the second template molecule is an analyte, drug, drug metabolite, amino acid, biological receptor, nucleic acid, steroid, immunosuppressant, hormone, heparin, antibiotics, vitamin, small pathological and disease biomarker, toxin, pesticide, herbicide, explosive, neurotoxin, endocrine disrupter, nucleotide, nucleoside, oligomeric nucleotide, or metabolon.

In one embodiment, the particle comprises a functionality at an outer layer of the particle.

In another embodiment, the functionality comprises an analyte capture or detection functionality.

In some embodiments, the functionality comprises a reporter for detection of an environmental change.

In other aspects, the present invention provides a method for preparing a molecularly imprinted molecule described herein.

In some embodiments, particles can be prepared using controlled condensation or additive radical "living" polymerization. The living free-radical polymerization techniques, such as reversible addition-fragmentation chain-transfer (RAFT) polymerization, iniferter polymerization, nitroxide-mediated radical polymerization, and atom-transfer radical polymerization (ATRP), can provide for the synthesis of particles comprising polymers with relatively controlled low-molecular weights. Without wishing to be bound by any particular theory, it is believed that controlled/living polymerization techniques can be based on a balance between dormant and active species that effectively reduces the concentration of propagating entities in the system and minimizes the extent of termination.

In some embodiments, the molecularly imprinted particle of the invention is prepared using RAFT polymerization, iniferter polymerization, nitroxide-mediated radical polymerization, or ATRP. In other embodiments, the molecularly imprinted particle of the invention is prepared using RAFT polymerization.

In one embodiment, the present invention provides a method for preparing a molecularly imprinted particle comprising a core formed by crosslinked polymer networks. The method comprises performing a RAFT polymerization of a composition to form the core, wherein the composition comprises a functional monomer susceptible to free-radical polymerization and a label. In one embodiment, the functional monomer is $C_2$-$C_8$ monoolefin, aromatic vinyl compounds, heterocyclic aromatic vinyl compounds, monoolefin type unsaturated carboxylic acid, carboxylate, ester and amide, vinyl alcohol or ester thereof, allyl alcohol or ester thereof, vinyl ether, vinyl lactam, vinyl halide, 1,1-dihaloethylene, (meth)acrylic acid or ester, salt, or amide thereof, 4-vinylpyridine, 2-vinylpyridine, 4-vinylbenzoic acid, (meth)acrylic acid, trifluoromethylacrylic acid, 2-hydroxyethyl methacrylate, dimethylaminoethyl methacrylate, (meth)acrylamide, 2-acrylamido-2-methylpropanesulfonic acid, 4-vinylimidazole, itaconic acid or N-vinylpyrrolidone.

In another embodiment, the functional monomer is 4-vinylpyridine, 2-vinylpyridine, 4-vinylbenzoic acid, (meth)acrylic acid, trifluoromethyl acrylic acid, 2-hydroxyethyl methylacrylate, dimethylaminoethyl methacrylate, (meth)acrylamide, 2-acry lamido-2-methy 1-1-propanesulfonic acid, 4-vinylimidazole, itaconic acid or N-vinylpyrrolidone.

In another embodiment, the functional monomer comprises a vinyl functional monomer.

In some embodiments, the functional monomer comprises N-tert-Butylmethacrylamide (tBMAm).

The label is as described herein.

In some embodiments, the label is a reversibly quenchable fluorescent label capable of transitioning into a non-fluorescent state, wherein the label can be (i) chemically quenched by an acid (e.g., hydrochloric acid (HCl)) or acidic buffer or environment; and (ii) chemically reactivated to its fluorescent state by e.g., a base (e.g., NaOH) or an alkaline buffer or environment.

In one embodiment, the label is Fluorescein-5-EX Succinimidyl ester.

In other embodiments, the composition further comprises a crosslinker, a chain transfer agent, and an initiator.

In some embodiments, the crosslinker comprises a monomer with two or more nonconjugated unsaturated double bond, preferably dial or polyol acrylate, methacrylate, allyl ether, or vinyl ether; the esters obtained from unsaturated monohydric alcohol or vinyl-containing $C_3$-$C_6$ carboxylic acid; the esters obtained from unsaturated carboxylic acid or polyol; linear or branched or cyclic aliphatic or aromatic alkanes with at least two double bond, wherein the double bond is nonconjugated in case of aliphatic alkane; diamine or polyamine acrylamide, methacrylamide, or N-allyl amine, more preferably ethylene glycol dimethacrylate (EGDMA), trimethylolpropane trimethacrylate, pentaerythritol triacrylate, divinylbenzene, N,N'-methylenebi sacrylamide, N,N'-ethylenebisacrylamide, N,N'-phenylbisacrylamide or 1,4-diacryloylpiperazine.

In one embodiment, the crosslinker comprises EGDMA.

In some embodiments, the chain transfer agent comprises a dithioester or trithiocarbonate organic compound. In another embodiment, the chain transfer agent comprises a thiocarbonylthio compound. In one embodiment, the chain transfer agent comprises 1-pyrrole carbothioic acid 2-cyano-2-propyl ester, 1-pyrrole carbothioic acid 2-cyano-2-butyl ester, 1-imidazole carbothioic acid benzyl ester, cumyl dithiobenzoate, cyanoisopropyl dithiobenzoate, 1-carboxyl isobutyl dithiobenzoate, S-1-dodecyl-S'-(a,a"-dimethyl-a"-acetic acid)trithiocarbonate, dodecy 1-S"-isopropanoic acid-trithiocarbonate, or a xanthate derivative (e.g., O-ethyl S-(1-phenylethyl)dithiocarbonate, O-ethyl S-(2-ethyloxycarbonyl-2-propyl)dithiocarbonate, or O-ethyl S-(2-cyanoisopropyl)dithiocarbonate).

In one embodiment, the chain transfer agent comprises a thiocarbonylthio moiety.

In another embodiment, the chain transfer agent comprises 4-cyano-4-(phenylcarbonothioylthio)pentanoic acid (CPDAB).

In some embodiments, said initiator is an azo-type free radical initiator, peroxide-type free radical initiator, or redox-type initiator, said azo-type free radical initiator is preferably selected from 2,2'-azobisisobutyronitrile, 2,2'azobi sisoheptonitrile, 2,2'-azobis(2-cyano-2-butane), 2,2'azobis(methyl isobutyrate), 4,4'-azobis(4-cyanovaleric acid), 4,4'-azobis(4-cyano-1-pentanol), 1,1'-azobis(cyano-cyclohexane), 2-tert-butylazo-2-cyanopropane, 2,2'-azobis{2-methyl-N-[1, 1-bis(hydroxymethyl)-2-hydroxyethyl] propionamide}, 2,2'-azobis[(2-methyl-N-hydroxyethyl)propionamide], bihydrochloride 2,2'-azobis(N,N'-bimethylene isobutyl amy), bihydrochloride 2,2'-azobis(2-amidinopropane), 2,2'-azobis(N,N'-bimethylene isobutylamine), 2,2'-azobis{2-methyl-N-[1, 1-bis(hydroxymethyl)-2-hydroxy-ethyl]propionamide}, 2,2'-azobis{2-methyl-N-[1, 1-bis(hydroxymethy 1)ethy 1]propionamide}, 2,2'-azobis[2-methyl-N-(2-hydroxyethyl)propionamide], dihydrate 2,2'-azobis(isobutyramide), 2,2'azobis(2,2,4-trimethylpentane), 2,2'-azobis(2-methylpropane); said peroxide type free radical initiator is preferably selected from tert-butyl peroxyacetate, tert-butyl peroxybenzoate, tert-butyl peroxy-2-ethyl-hexanoate, tertbutyl peroxyneodecanoate, tert-butyl perisobutyrate, tertamyl perpivalate, tert-butyl peroxypivalate, diisopropyl peroxydicarbonate, dicyclohexyl peroxydicarbonate, dicumyl peroxide, benzoyl peroxide, dilauroyl peroxide, potassium persulfate, ammonium persulfate, di-tert-butyl hyponitrite, di-t-butyl peroxide or p-dipropyl-benzene hyponitrite, cumyl hydroperoxide, tert-butyl hydroperoxide; for said redox type free radical initiator, wherein the oxidants include organic (alkyl-, aryl-, acyl-) hydrogen peroxide, persulfate, superphosphate, organic peroxide, preferred oxidants include persulfate and organic hydrogen peroxide, and the preferred oxidants include ammonium, sodium, or potassium persulfate, tert-butyl hydroperoxide, reducing agents include sodium formaldehyde sulfoxylate, sodium sulfite, sodium metabisulfite, sodium dithionite, ascorbic acid, D-isoascorbic acid, hydrazine, hydroxylamine or its salt, reducing sugar, mercaptan, and sulfonic acid derivatives, aluminumtriethyl, triethylborane, tertiary amine, preferred reducing agents include sodium formaldehyde sulfoxylate, sodium metabisulfite, D-isoascorbic acid, sodium hydrosulfite, sodium thiosulfate, sodium sulfite, and the preferred reducing agent is sodium dithionite.

In one embodiment, the initiator is potassium persulfate (KPS).

In other embodiments, the composition further comprises a second crosslinker.

In one embodiment, the second crosslinker comprises N,N'-Methylenebisacrylamide (BIS).

In other embodiments, the method further comprising polymerizing a second monomer in the presence of the core to form a polymeric shell at least partially surrounding the core.

In one embodiment, the second monomer comprises N-methacryloyl-6-aminohexanoic acid (MA6AHA).

In some embodiments, a polymerization solvent is water, acetonitrile, acetonitrile/toluene, acetonitrile/tetrahydrofuran, acetonitrile/methanol, acetonitrile/ethanol, acetonitrile/propanol, acetonitrile/butanol, acetonitrile/pentanol, methanol, ethanol, propanol, butanol, pentanol, methanol/water, ethanol/water, propanol/water, butanol/water, pentanol/water, toluene, tetrahydrofuran, N,N-dimethyl-formamide, dimethyl sulfoxide, 2-butanone or liquid paraffin.

In another embodiment, the molar ratio of the template, functional monomer, and crosslinker is 1:1-10:4-80, 1:1-9:4-70, 1:1-8:4-50, 1:1-6:4-10, or 1:1-4:4-10.

In some embodiments, the molar ratio of the total amount of the functional monomer and crosslinker to that of the chain transfer agent is 500:1-10:1, 200:1-10:1, 150:1-50:1, or 150:1-80: 1.

In other embodiments, the method further comprising providing a functionality to an outer layer of the particle. In one embodiment, the outer layer is an outer surface of the polymeric shell.

In some embodiments, the functionality, and method for providing the functionality, can be as described herein.

In one embodiment, the functionality comprises an analyte capture or detection functionality. In another embodiment, the functionality comprises a reporter for detection of an environmental change.

In some embodiments, the molecularly imprinted particle is prepared by RAFT polymerization in one-pot.

In other aspects, the present invention provides a particle prepared by the methods described herein e.g., prepared by a RAFT polymerization, in particular a one-pot RAFT polymerization.

In other aspects, the present invention provides a composition comprising the molecularly imprinted particles described herein.

In still further aspects, the present invention provides a kit comprising the molecularly imprinted particles described herein, along with instructions for use.

In other aspects, the present invention provides a method for capturing or detecting an analyte. The method comprises contacting the analyte with a particle of the invention, wherein the particle comprises a functionality at an outer layer of the particle for capturing or detecting the analyte.

In some embodiments, the method is a high throughput screening method.

In one embodiment, the analyte is a drug.

In some aspects, the present invention provides a method for detecting an environmental change. The method comprises exposing a particle of the invention to the environmental change, wherein the particle comprises a functionality at an outer layer of the particle, wherein the functionality comprises a reporter for detection of the environmental change.

In one embodiment, the environmental change comprises a change in pH.

The invention will be further described in the following examples, which do not limit the scope of the invention described in the claims.

EXAMPLES

Example 1

Core synthesis

Reversible addition-fragmentation chain transfer (RAFT) precipitation polymerization was used to generate the core particles used in this study. RAFT reaction was prepared by adding 160 mL of HPLC-grade water (HPLC grade $H_2O$) to a large glass jar with a football stir bar and stirred on a magnetic stir plate to create a vortex. N-tert-Butylmethacrylamide (tBMAm, 12.2 mmol) and N,N'-Methylenebisacrylamide (BIS, 0.675 mmol) were added, and the jar capped, to stir overnight at room temperature. For fluorescent microparticles, Fluorescein-5-EX, Succinimidyl Ester from Thermo was added (Fluorescein, 4.24 µmol) after tBMAm and BIS addition, the jar capped, and reaction left to stir overnight at room temperature.

For each reaction, a new Millipore stericup-steritop vacuum filter (0.22 µM) was used to filter the solution into a 500 mL round bottom flask (RBF) with another football stir bar. Every RBF used in the reactions are cleaned thoroughly with acid and base bath (1 kg Potassium Hydroxide in a solution of 16 L isopropanol and 4 L distilled water), washed several times with HPLC-grade $H_2O$, Acetone (100%), and then oven dried. The glass jar was quantitatively washed with 30, 35, 35 and 100 mL of HPLC grade $H_2O$ to transfer all the material to the RBF for a final 360 mL reaction volume. 1,3,5-trioxane (12.0 mmol) was added to the RBF and kept stirring at 150 rotations per minute (RPM). 0.200 mL of the solution in the RBF was set aside as the 0 hour sample.

Ethylene glycol dimethacrylate (EGDMA, 0.675 mmol), 4-cyano-4-(phenylcarbonothioylthio)pentanoic acid (CP-DAB, 0.180 mmol), potassium persulfate (KPS, 0.0540 mmol) were added to each RBF, sealed with a clean rubber septum and electrical tape. Two 4-inch, 22-gauge, needles were inserted through the septum, with one immersed in solution and connected to a nitrogen source and left to sparge the solution for two hours at room temperature. Each RBF was then placed in another pre-heated VWR stir-plate oil baths at 76° C., and left stirring at 150 RPM for 30 minutes. The temperature of the oil baths was set to 73° C. for 20 minutes, 72° C. for 10 minutes, 70° C. for 10 minutes, and finally left at 70° C. for 24 hours. 50 mL of the solution in each RBF was set aside as the 24-hour sample.

After each RBF was left to cool at room temperature for 30 minutes, solutions were transferred to dialysis membranes (10 000 MWCO) and tied at both ends. The bags were immersed in $H_2O$ with Hydrochloric acid (HCl, 2.00 mmol) for dialysis of 360 mL of the solution to obtain a ~53 200-fold dilution in the dialysis buffer. Fluorescent and non-fluorescent microparticles were dialyzed in separate containers. After dialysis, 0.200 mL of the solution in the RBF was set aside as the post-dialysis sample. The dialyzed cores were stored in glass bottles at 4° C. for further characterization and use for core-shell synthesis.

Example 2

Preparation of Core-shells

A 100 mL RBF (cleaned as described in Example 1) was prepared with a (football medium) magnetic stir bar. 36 mL of HPLC-grade $H_2O$, along with N-methacryloyl-6-aminohexanoic acid (MA6AHA, 1.19 mmol), BIS (120 μmol), Trioxane (2.00 mmol) were added into the solution to mix. Then 24 mL of cores made previously were transferred to the RBF and allowed to mix. 0.200 mL of the solution in the RBF was set aside as the 0-hour core-shell sample. Then, KPS was added (2.40 nmol) before sparging the solution under Nitrogen for 60 minutes at room temperature as described above. Before the first ten minutes of immersing the RBF, the temperature of the stir plate reported by the probe was confirmed via a separate alcohol thermometer suspended into the oil bath. The RBF was then transferred to the VWR-stir plate oil bath at 70° C. for 12 hours at a 300 RPM stir rate. The temperature of the oil bath was monitored for the first hour of the reaction at 0-, 40-, 50- and 60-minute time points.

After the 12 hours, the RBF was cooled to room temperature, 0.200 mL of the solution was set aside as the 24-hour sample. Then, 30 mL was transferred to dialysis tubing (10000 MWCO) for dialysis in $H_2O$ with Hydrochloric acid (HCl, 2.00 mmol) to obtain a ~2.8E8 fold dilution in the dialysis buffer.

The remaining ~30 mL of the core-shell reaction was transferred to a 50 mL conical centrifuge tube to be spun down at 4° C., and 4500 g force, in a table top centrifuge to separate the supernatant and the pellet fractions for fluorescence intensity reads. Pellets were resuspended in 30 mL of 10 mM Tris-HCl, pH 7.4 buffer before being used in fluorescence assays.

Example 3

Fluorescence Quenching Assays

100 μL of the sample being analyzed was placed in triplicate in a Greiner black, top-read, 96-well plate with flat bottom. The plate was read using a Biotek Cytation 5 plate reader and monochromator at 488/519 nM wavelength for excitation and emission detection of Fluorescein fluorophore.

Kinetic assays were performed after a 10 second shake, for 20-minute durations, at 17 reads per well, and 1:12 minutes per read. After establishing the baseline read, 15 μL Sodium Hydroxide (NaOH, 1M or 2M) was added to each well to activate the pre-quenched fluorescein embedded in the core. The 20-minute kinetic assay was repeated. Then, 15 μL of Hydrochloric acid (HCl, 1M or 2M) was added to each well to quench the fluorophore. After another 20-minute kinetic assay was recorded, the NaOH and HCl addition steps were repeated with kinetic reads in between to measure the reversibility of fluorescence intensity of the fluorescent microparticles. Data was normalized by averaging the fluorescence reads of the blank row and subtracting the value from the sample value using Cytation software version 3.03.14. The resulting triplicate reads were graphed using GraphPad Prism 5.0 and error bars shown are Standard Deviation (SD) from the mean of the triplicates.

Figure 1:
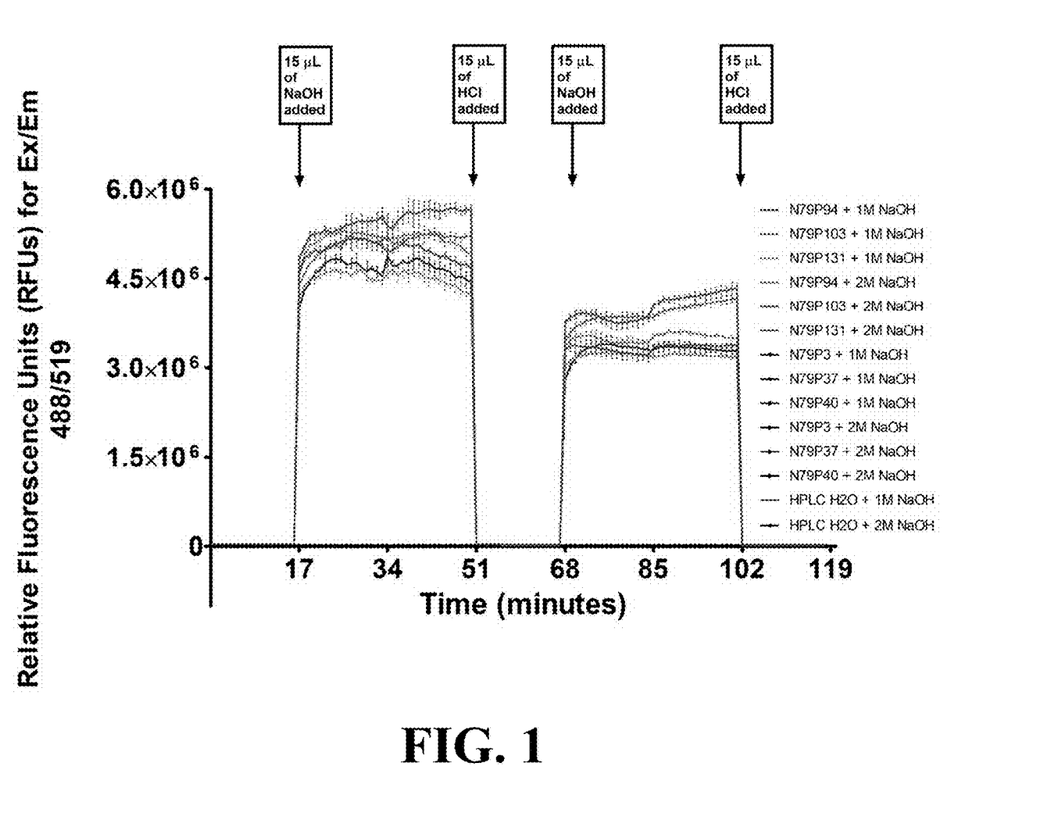
FIG. 1 is a graph showing reversible quenching states of fluorescent and non-fluorescent microparticles with indications of 1-2 M HCl or 1-2 M NaOH added at 20-minute intervals.

The results of reversible quenching states of fluorescent and non-fluorescent microparticles with indications of 1-2 M HCl or 1-2 M NaOH added at 20-minute intervals are shown in FIG. 1. Baseline fluorescence of fluorescent microparticles was higher than non-fluorescent microparticles. Fluorescent microparticles showed greater quenching upon 15 μL of 1M HCl addition compared to non-fluorescent microparticles. Adding 15 μL of 1 M NaOH dramatically increased fluorescence of fluorescent microparticles, displaying high degree of reversible quenching of fluorescent microparticles. In contrast, non-fluorescent microparticles were not reversibly quenchable.

Figure 2:
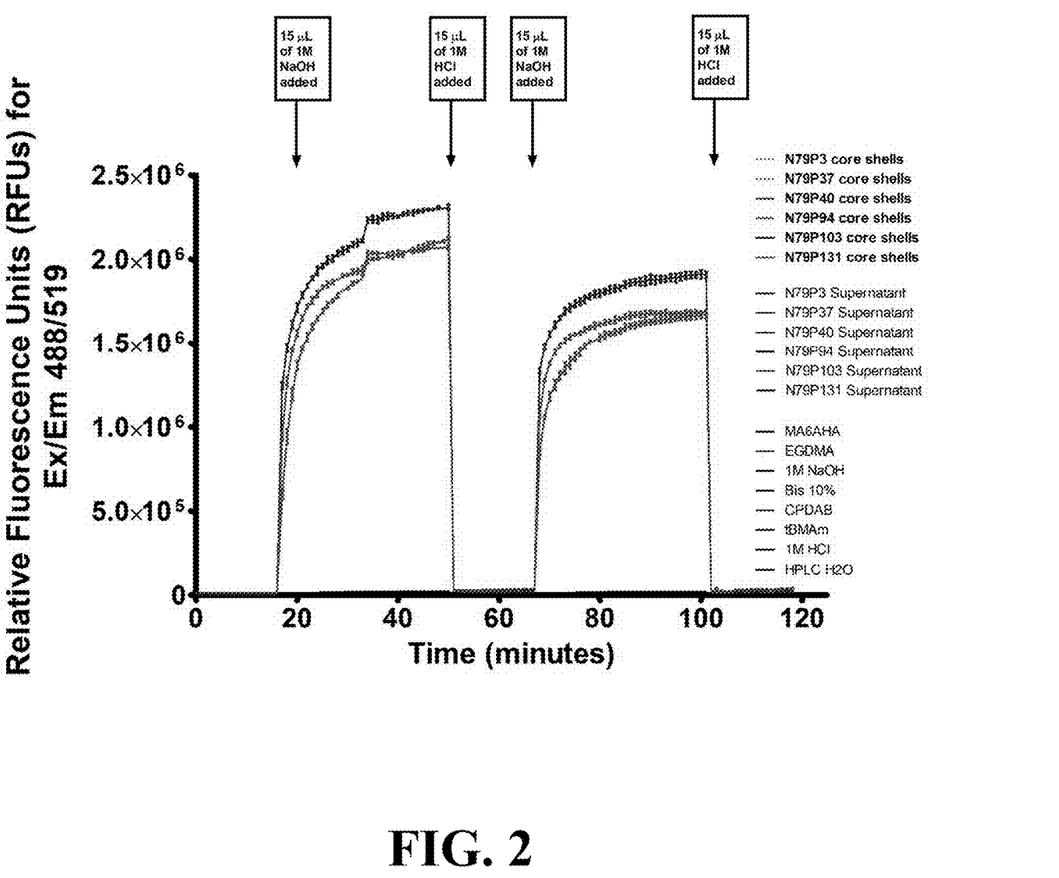
FIG. 2 is a graph showing fluorescence kinetic assays on fluorescent and non-fluorescent core-shells, core-shell reaction supernatants, and core/core-shell reagents.

The results of reversible quenching states of fluorescence kinetic assays on fluorescent and non-fluorescent core-shells, core-shell reaction supernatants, and core/core-shell reagents are shown in FIG. 2. Fluorescent core-shell microparticles exhibited reversible quenching and fluorescence activation behavior shown by the addition of NaOH and HCl at 1 M concentrations. Supernatants from each of the core-shell reactions, non-fluorescent core-shell microparticles, as well as the reagents used for core and core-shells syntheses all displayed baseline levels of fluorescence intensity seen in the water control. This indicates that there are negligible amounts of fluorophore leakage from the molecularly imprinted particles during and after the core and core- shell synthesis procedures that require the fluorescent particles to be heated up to 76° C. for 30 minutes, 73° C. for 20 minutes, 72° C. for 10 minutes, 70° C. for 10 minutes, and 70° C. for 12-24 hours.

Example 4

Dynamic Light Scattering (DLS) On Cores Using Multi Angle Light Scattering (MALS)

1.5 μL of the sample being analyzed was added to 3 mL of HPLC-grade H20 in a clear plastic cuvette, capped, and gently inverted to mix. The cuvette was placed in a Beckman Coulter N5 Submicron Particle Size Analyzer for determination of the statistical average particle diameter using an empirically determined diffusion coefficient and the Stokes-Einstein equation (Patanarut, A.; Luchini, A.; Botterell, P.J.; Mohan, A.; Longo, C.; Vorster, P.; Petricoin III, E.F.; Liotta, L.A.; Bishop, B. *Colloids Surf., A* 2010, 362, 8-19.). The diluent was set to water, with a refractive index (RI) of 0.692, and a diluent viscosity (cP) of 1.331 at 37° C. Each sample was analyzed at 11.1°, 15.7°, 23.0°, 30.2°, 62.6°, and 90.0° angles with ten repetitions per angle, 5-minute equilibration time, and 85 second run time.

Figure 3:
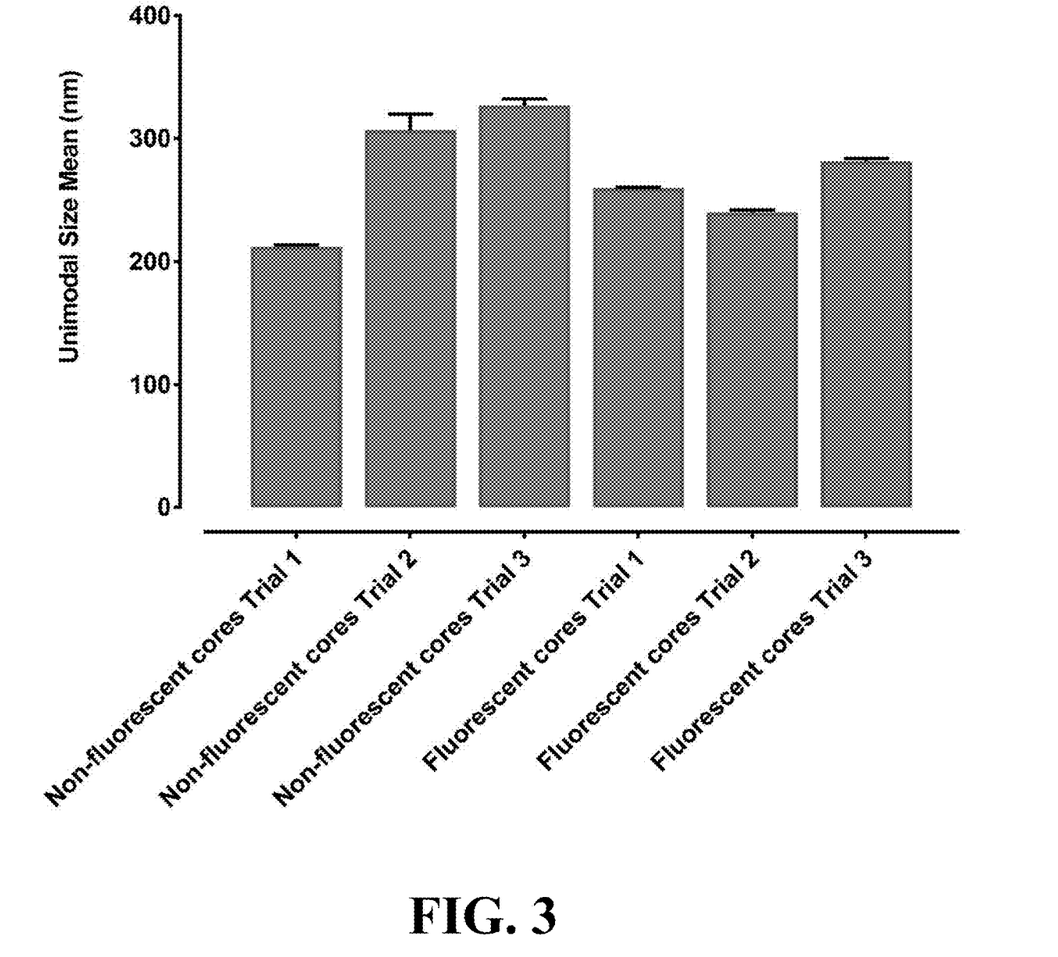
FIG. 3 is a graph showing average diameter (nm) per core synthesis at a 90° angle and 25° C. temperature, 3 technical repetitions per sample.

Average diameter (nm) per core synthesis at a 90° angle and 25° C. temperature, 3 technical repetitions per sample, is shown in FIG. 3. Summary of average microparticle diameters for core syntheses used in this study is shown in Table 1.

TABLE 1

Summary of average microparticle diameters for core syntheses used in this study

| Core synthesis reaction | Average diameter (nm) | $\sigma_{dev}$ |
|---|---|---|
| Non-fluorescent cores Trial 1 | 212.24 | 1.37 |
| Non-fluorescent cores Trial 2 | 306.90 | 4.35 |
| Non-fluorescent cores Trial 3 | 326.85 | 1.88 |
| Fluorescent cores Trial 1 | 259.76 | 0.29 |
| Fluorescent cores Trial 2 | 240.30 | 1.38 |
| Fluorescent cores Trial 3 | 281.72 | 1.36 |

Figure 4:
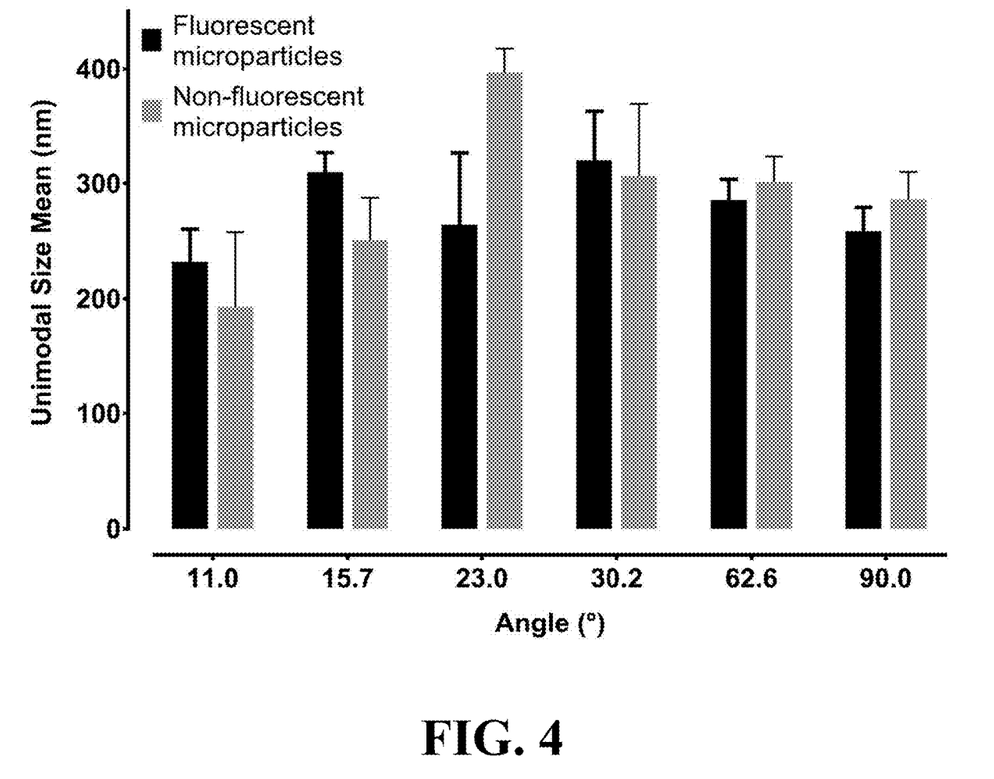
FIG. 4 is a graph showing DLS MALS studies (all six angles, 37° C.) of fluorescent cores compared to regular cores from RAFT polymerization.

The results of DLS MALS studies (all six angles, 37° C.) of fluorescent cores compared to regular cores from RAFT polymerization are shown in FIG. 4. Each of the reported data points consist of three separate core syntheses done respectively for fluorescent and non-fluorescent microparticles. Summary of MALS studies done on fluorescent and non-fluorescent microparticles is shown in Table 2 where each reported average contains 30 repetitions, where each of the three core synthesis carried out separately were assessed with ten technical DLS repetitions each.

TABLE 2

Summary of MALS studies done on fluorescent and non-fluorescent microparticles

| A | 11° | $\sigma_{dev}$ | 15.7° | $\sigma_{dev}$ | 23° | $\sigma_{dev}$ | 30.2° | $\sigma_{dev}$ | 62.6° | $\sigma_{dev}$ | 90° | $\sigma_{dev}$ |
|---|---|---|---|---|---|---|---|---|---|---|---|---|
| B | 192.71 | 64.70 | 250.84 | 35.94 | 396.69 | 20.01 | 306.46 | 63.15 | 301.57 | 22.05 | 286.15 | 23.25 |
| C | 232.05 | 27.60 | 310.19 | 16.33 | 264.15 | 62.19 | 320.85 | 41.95 | 285.74 | 17.74 | 258.58 | 20.65 |

Row A: Angle (°);
Row B: Diameter of non-fluorescent microparticles (nm);
Row C: Diameter of fluorescent microparticles (nm).

The results of Dynamic Light Scattering (DLS) swelling studies of fluorescent and non- fluorescent cores using temperature variation protocol with ten repetitions per core synthesis (total of 3 syntheses reported per dataset) are shown in Table 3.

TABLE 3

Dynamic Light Scattering (DLS) swelling studies of fluorescent and non-fluorescent cores using temperature variation protocol with ten repetitions per core synthesis (total of 3 syntheses reported per dataset).

| Temperature (° C.) | Average diameter of non-fluorescent microparticles (nm) | $\sigma_{dev}$ | Average diameter of Fluorescent microparticles (nm) | $\sigma_{dev}$ |
|---|---|---|---|---|
| 25° C. | 282.00 | 51.39 | 260.59 | 17.99 |
| 30° C. | 277.69 | 49.57 | 260.97 | 19.28 |
| 35° C. | 273.06 | 45.58 | 260.04 | 20.67 |
| 40° C. | 274.20 | 43.13 | 239.72 | 13.09 |
| 50° C. | 262.37 | 46.21 | 234.40 | 7.32 |

Figure 5:
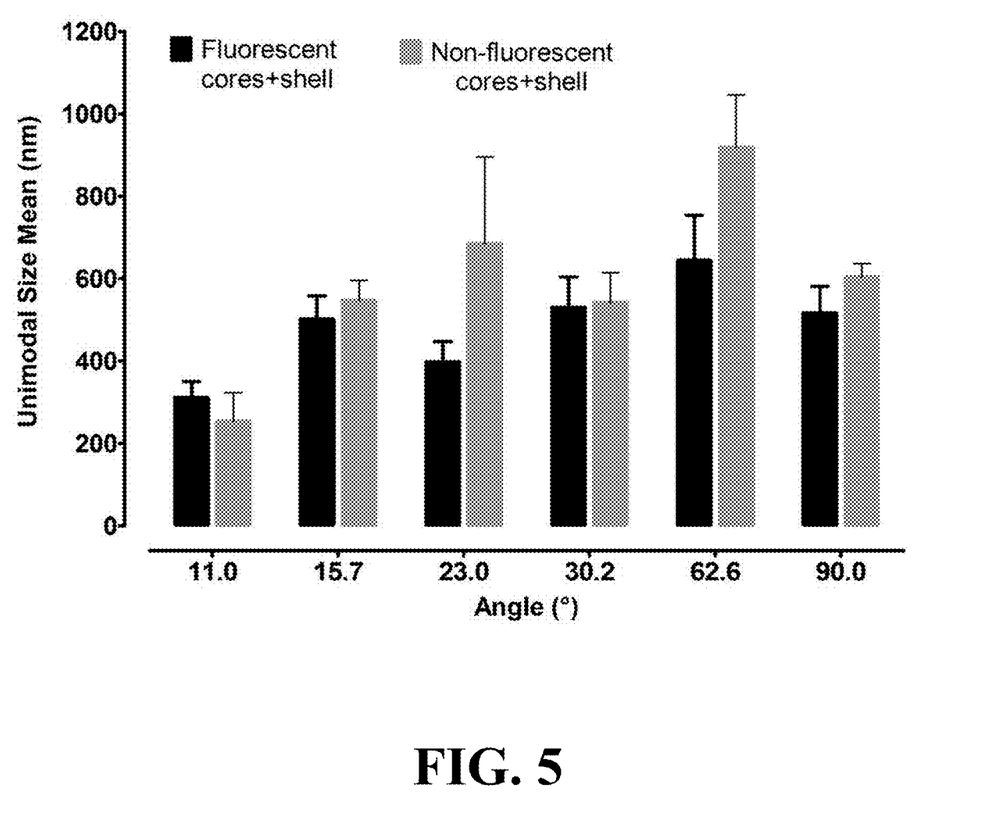
FIG. 5 is a graph showing DLS MALS studies (all six angles, 37° C.) of fluorescent and non-fluorescent core-shells.

The results of DLS MALS studies (all six angles, 37° C.) of fluorescent and non-fluorescent core-shells are shown in FIG. 5. Each of the reported data point consists of three separate core synthesis done respectively for fluorescent and non-fluorescent microparticles. Non-fluorescent core-shells display a larger diameter compared to fluorescent core-shells.

Example 5

Dynamic Light Scattering (DLS) On Cores Using Varying Temperatures

Samples were prepared similar to MALS assays, using water as the diluent. Each sample was analyzed at 25.0° C. (diluent RI of 0.890, cP of 1.333), 30.0° C. (diluent RI of 0.797, cP of 1.332), 35.0° C. (diluent RI of 0.719, cP of 1.331), 40.0° C. (diluent RI of 0.653, cP of 1.331), and 50.0° C. (diluent RI of 0.547, cP of 1.329) temperatures. All temperature analyses were performed at a 90.0° angle with three repetitions per temperature, 5-minute equilibration time, and 200 second run time.

Figure 6:
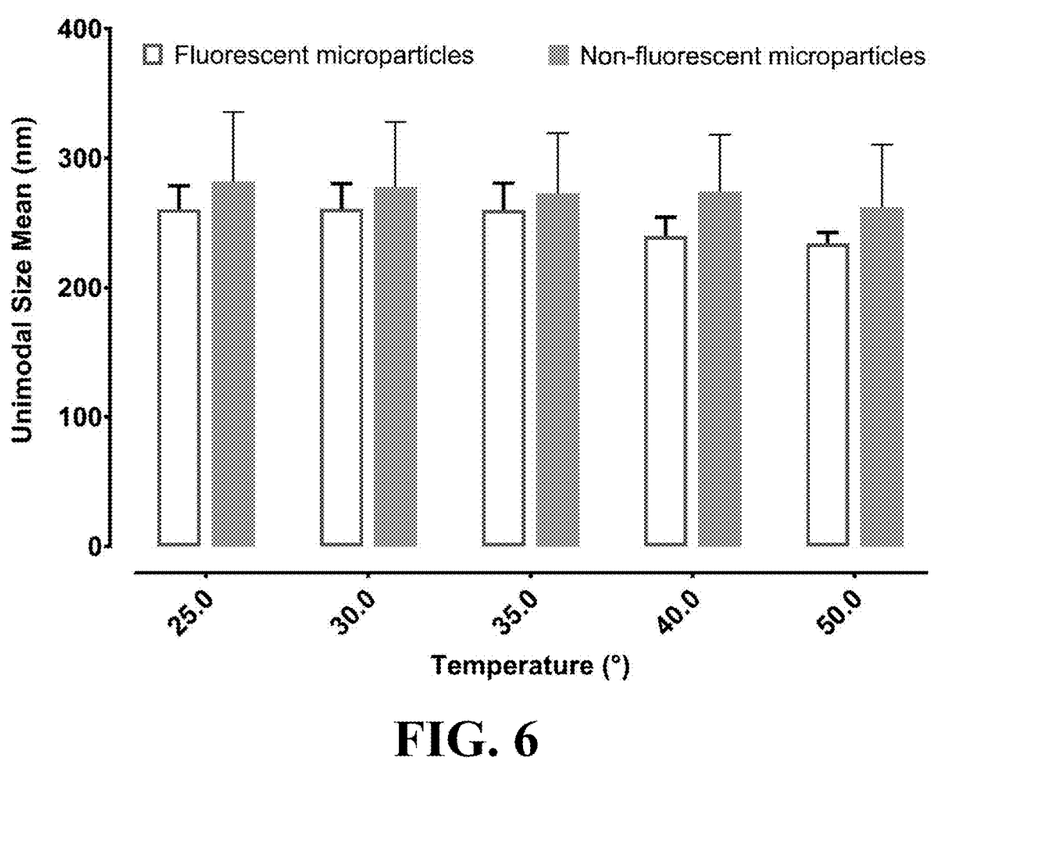
FIG. 6 is a graph showing DLS swelling studies done at a 90° angle, and with 25° C.-50° C. temperatures. Average of 3 separate fluorescent core syntheses (white bars) are compared to the average of 3 separate non-fluorescent core syntheses. Fluorescent cores are slightly smaller than non-fluorescent cores across 25° C.-50° C. temperature range. Both types of cores shrink slightly with increasing temperatures but are otherwise temperature independent with regard to diameter.

The results of DLS swelling studies done at a 90° angle, and with 25° C.-50° C. temperatures are shown in FIG. 6. Average of 3 separate fluorescent core syntheses (white bars) are compared to the average of 3 separate non-fluorescent core syntheses. Fluorescent cores were slightly smaller than non-fluorescent cores across 25° C-50° C. temperature range. Both types of cores shrank slightly with increasing temperatures but were otherwise temperature independent with regard to diameter.

Figure 7:
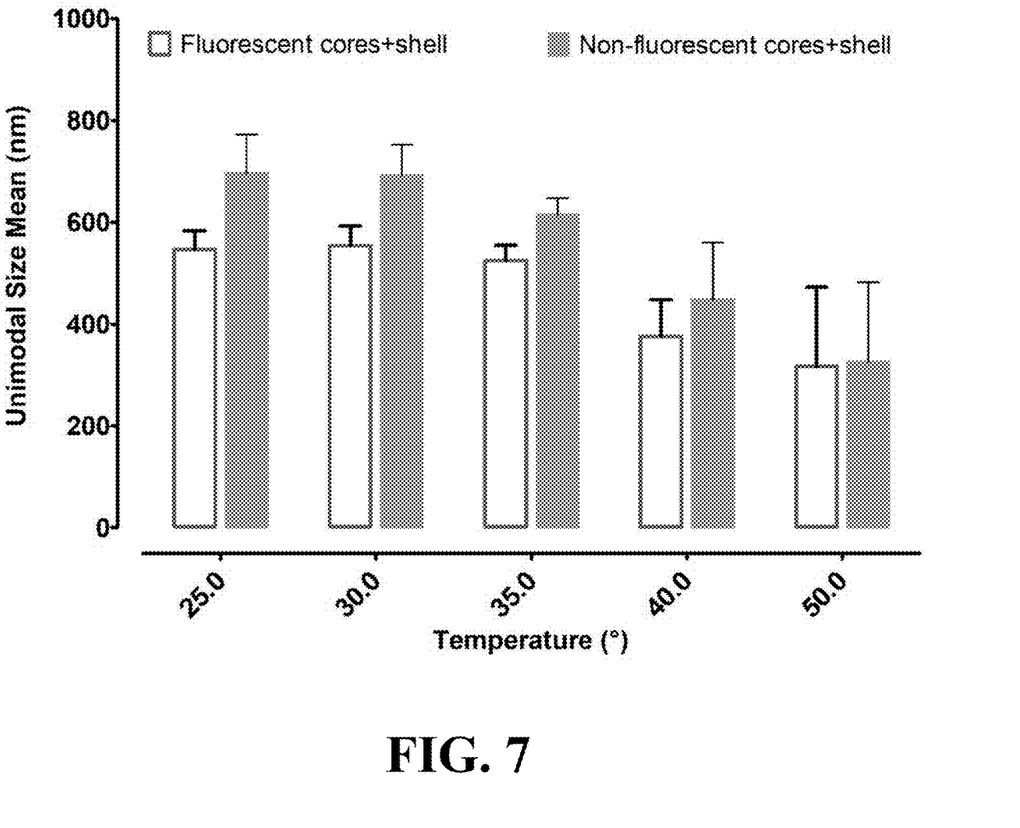
FIG. 7 is a graph showing DLS swelling studies of fluorescent and non-fluorescent core-shells done at a 90° angle, and with 25° C. -50° C. temperatures. Average of 3 separate fluorescent core-shell syntheses (white bars) are compared to the average of 3 separate non-fluorescent core-shell syntheses.

The results of DLS swelling studies of fluorescent and non-fluorescent core-shells done at a 90° angle, and with 25° C. -50° C. temperatures are shown in FIG. 7. Average of 3 separate fluorescent core-shell syntheses (white bars) are compared to the average of 3 separate non-fluorescent core-shell syntheses. Fluorescent core-shells were slightly smaller than non-fluorescent core-shells across 25° C. -50° C. temperature range. Both types of core-shells shrank with increasing temperatures and are expectedly temperature dependent with regard to diameter.

Example 6

Nuclear Magnetic Resonance Spectroscopy $^1$H-1-1D spectra of cores and core-shell microparticles were collected on a 400 MHz Bruker Avance spectrometer using a 5 mm glass NMR tube and 0.550 mL sample volume. 0.500 mL of each sample was transferred to a microcentrifuge tube, 0.050 mL of 99.9% Deuterium Oxide (D20, Cambridge Isotope Labs) added, and the resulting solution vortexed before being transferred to the NMR tube. All spectra were collected using Bruker ZGGPWG pulse sequence for water suppression (M. Piotto, V. Saudek & V. Sklenar, J. Biomol. NMR 2, 661 - 666 (1992), V. Sklenar, M. Piotto, R. Leppik V. Saudek, J. Magn. Reson.,Series A 102, 241 -245 (1993)).

Spectra were processed for phasing and baseline correction using Avance Top Spin software version 3.5. Processed spectra were then analyzed using Top Spin software version 3.5 to generate peak lists for MA6AHA, Trioxane and BIS. The area under each peak was then integrated, and the data analyzed for MA6AHA and BIS peak values with reference to Trioxane peaks using the following formula: Overall Peak intensity with reference to the trioxane peak at $[(t_0-t_{24})/t_0]$. For core shells ratios, the following formula was used: Ratio of BIS or MA6AHA peaks=Peak intensity with reference to the trioxane peak at $[(t_0-t_{12})/t_0]$.

The NMR-derived non-fluorescent microparticle values of integrated peak ratios relative to Trioxane peaks are shown in Table 4.

TABLE 4

NMR-derived non-fluorescent microparticle values of integrated peak ratios relative to Trioxane peaks

| N79P3CS | MA6AHA | MA6AHA | MA6AHA | bis | bis |
|---|---|---|---|---|---|
| signal | 5.35 | 5.60 | 1.90 | 5.72 | 6.17 |
| t0 | n/a | 43.83 | 2751.46 | 18.15 | 142.63 |
| t12 | n/a | 25.89 | 1149.21 | 7.19 | 54.71 |
| t0 − t12/t0 | n/a | 0.41 | 0.58 | 0.60 | 0.62 |
| Average | n/a | 0.50 | | 0.61 | |

| N79P40CS | MA6AHA | MA6AHA | MA6AHA | bis | bis |
|---|---|---|---|---|---|
| signal | 5.35 | 5.60 | 1.90 | 5.72 | 6.17 |
| t0 | 8.31 | 32.70 | 1526.13 | 12.39 | 55.98 |
| t12 | 3.41 | 9.33 | 444.35 | 5.41 | 20.87 |
| t0 − t12/t0 | 0.59 | 0.71 | 0.71 | 0.56 | 0.63 |
| Average | 0.67 | 0.71 | | 0.60 | |

TABLE 4-continued

NMR-derived non-fluorescent microparticle values of integrated peak ratios relative to Trioxane peaks

| N79P37CS | MA6AHA | MA6AHA | MA6AHA | bis | bis |
|---|---|---|---|---|---|
| signal | 5.35 | 5.60 | 1.90 | 5.72 | 6.17 |
| t0 | 5.41 | 30.46 | 1382.92 | 12.63 | 53.88 |
| t12 | 2.54 | 11.50 | 558.81 | 5.88 | 26.41 |
| t0 – t12/t0 | 0.53 | 0.62 | 0.60 | 0.53 | 0.51 |
| Average | 0.58 | 0.61 | | 0.52 | |

The NMR-derived fluorescent microparticle values of integrated peak ratios relative to Trioxane peaks are shown in Table 5.

TABLE 5

NMR-derived fluorescent microparticle values of integrated peak ratios relative to Trioxane peaks

| N79P131CS | MA6AHA | MA6AHA | MA6AHA | bis | bis |
|---|---|---|---|---|---|
| signal | 5.35 | 5.60 | 1.90 | 5.72 | 6.17 |
| t0 | 5.60 | 22.00 | 1217.08 | 6.84 | 45.96 |
| t12 | 4.39 | 19.27 | 1052.19 | 4.92 | 35.58 |
| t0 – t12/t0 | 0.22 | 0.12 | 0.14 | 0.28 | 0.23 |
| Average | 0.16 | 0.13 | | 0.25 | |

| N79P103CS | MA6AHA | MA6AHA | MA6AHA | bis | bis |
|---|---|---|---|---|---|
| signal | 5.35 | 5.60 | 1.90 | 5.72 | 6.17 |
| t0 | 6.00 | 27.09 | 1283.31 | 8.91 | 61.93 |
| t12 | 1.83 | 10.53 | 495.12 | 2.96 | 26.45 |
| t0 – t12/t0 | 0.69 | 0.61 | 0.61 | 0.67 | 0.57 |
| Average | 0.64 | 0.61 | | 0.62 | |

| N79P94CS | MA6AHA | MA6AHA | MA6AHA | bis | bis |
|---|---|---|---|---|---|
| signal | 5.35 | 5.60 | 1.90 | 5.72 | 6.17 |
| t0 | 7.13 | 18.41 | 1021.31 | | 51.10 |
| t12 | 4.09 | 9.32 | 637.49 | | 22.63 |
| t0 – t12/t0 | 0.43 | 0.49 | 0.38 | #DIV/0! | 0.56 |
| Average | 0.43 | 0.43 | | #DIV/0! | |

Although molecular imprinting is used in several polymerization pathways, none have used a one-pot Reversible Addition-Fragmentation chain Transfer (RAFT) synthesis that incorporates molecular imprinting of a fluorophore to create fluorescent microparticles. A reversibly quenchable, fluorescent, microparticle system using a one-pot RAFT polymerization reaction was prepared. Dynamic Light Scattering (DLS) swelling studies showed that the diameter of the fluorescent microparticles were only slightly affected by variations in temperatures, similar to previously engineered non-fluorescent RAFT microparticles. While using fluorescent microparticles in core-shell reactions performed at 70° C. for 12 hours, no fluorophore leakage was detected, and fluorescence intensities of fluorescent core-shell microparticles were preserved for particles in storage for up to 3 to 4 months in 4° C. (not shown). Nuclear Magnetic Resonance (NMR) spectroscopy displayed the lack of any free fluorescein in fully dialyzed microparticle preparations, even though ratios of BIS incorporation were significantly lower than non-fluorescent core-shell preparations. Multi Angle Light Scattering (MALS) assays of cores and core-shells showed the expected increase in diameter, with fluorescent core-shells being more compact in diameter.

The versatile applications of the fluorescent microparticles were demonstrated in kinetic fluorescence assays that showed the reversible quenching of the fluorescent microparticles in the presence and absence of added MA6AHA shell layers on their surface. This core-shell addition on microparticles can be exchanged for other systems as needed by the user for fluorescence-based validation of polymer coverage on microparticles. Incorporation of encapsulating polymeric hydrogel outer layers can be used to introduce new functionality into the fluorescent microparticles, and allow their adaptation for a variety of applications, including analyte capture and detection. The fluorescent core allows fluorescent particle sorting, cost-efficient imaging for visualizing particles, reporters for environmental changes, as well as a means of detecting and quantifying the particles. Further, the fluorescent ligand used in this study, namely Fluorescein-5-EX Succinimidyl Ester, can be exchanged for other fluorophores without having to engineer fluorophore-specific polymerization pathways.

We claim:

1. A method for preparing a particle comprising a core, comprising crosslinked polymer networks attractively associated with a fluorescent label, the method comprising:
performing a reversible addition-fragmentation chain transfer (RAFT) polymerization of a composition comprising a vinyl functional monomer and a crosslinker in the presence of the fluorescent label, wherein:
 (a) the vinyl functional monomer is selected from the group consisting of an acrylamide, a methacrylamide, an acrylate, and a methacrylate;
 (b) the crosslinker is selected from the group consisting of a diamine acrylamide, diamine methacrylamide, polyamine acrylamide, polyamine methacrylamide, diol acrylate, diol methacrylate, polyol acrylate, and polyol methacrylate;
 (c) the fluorescent label is selected from the group consisting of fluorescein-5-EX N- hydroxysuccinimide ester, 2',71'-dichlorofluorescein diacetate, 5(6)-carboxyfluorescein diacetate, 5(6)-carboxyfluorescein diacetate N-succinimidyl ester, 5-(bromomethyl)fluorescein, 5-(iodoacetamido) fluorescein, 5-([4,6-dichlorotriazin-2-yl]amino)fluorescein hydrochloride, 5-carboxy-fluorescein diacetate N-succinimidyl ester, 5-carboxyfluorescein, 5-carboxyfluorescein N-succinimidyl ester, 6-carboxy-fluorescein diacetate N-succinimidyl ester, 6-[fluorescein-5(6)-carboxamido]hexanoic acid, 6-[fluorescein-5(6)-carboxamido]hexanoic acid N-hydroxysuccinimide ester, 6-carboxy-4',5'-dichloro-2',7'-dimethoxyfluorescein N-hydroxysuccinimide ester, 6-carboxyfluorescein, eosin Y disodium salt, fluorescein (free acid), fluorescein 5(6)-isothiocyanate, fluorescein diacetate 5(6)-isothiocyanate, fluorescein diacetate 5-maleimide, fluorescein diacetate 6-isothiocyanate, fluorescein isothiocyanate isomer I, fluorescein sodium salt, fluorescein-5-EX N-hydroxysuccinimide ester, fluorescein-O'-acetic acid, and O'-(carboxymethyl)fluoresceinamide; and
 (d) the attractive association is selected from the group consisting of an electrostatic, hydrophobic, and hydrogen-bonding interaction.

2. The method of claim 1, wherein the composition further comprises a chain transfer agent and an initiator.

3. The method of claim 1, wherein the composition further comprises a second crosslinker.

4. The method of claim 1, further comprising polymerizing a second vinyl functional monomer to form a polymeric shell at least partially surrounding the particle.

5. The method of claim 1, further comprising providing a functionality to an outer layer of the particle.

6. The method of claim 1, wherein the vinyl functional monomer is N-tert-Butylmethacrylamide (tBMAm), and wherein the crosslinked polymer network comprises crosslinked units of the N-tert-Butylmethacrylamide (tBMAm).

7. The method of claim 5, wherein the functionality comprises analyte capture or detection.

8. The method of claim 4, wherein the polymeric shell comprises crosslinked units of the second vinyl functional monomer.

9. The method of claim 8, wherein the second vinyl functional monomer comprises N-methacryloyl-6-aminohexanoic acid (MA6AHA).

10. The method of claim 2, wherein the crosslinker comprises ethylene glycol dimethacrylate (EGDMA).

11. The method of claim 3, wherein the second crosslinker comprises N,N'-Methylenebisacrylamide (BIS).

12. The method of claim 1, wherein the core has a core diameter of about 500 nm or less.

\* \* \* \* \*